United States Patent [19]

Takamura et al.

[11] 4,407,907
[45] Oct. 4, 1983

[54] AIR ELECTRODE

[75] Inventors: Tsutomu Takamura, Yokohama; Yuichi Sato, Atsugi; Toshiaki Nakamura, Yono; Nobukazu Suzuki, Tokyo, all of Japan

[73] Assignee: Tokyo Shibaura Denki Kabushiki Kaisha, Kawasaki, Japan

[21] Appl. No.: 325,753

[22] Filed: Nov. 30, 1981

[30] Foreign Application Priority Data

Dec. 23, 1980 [JP] Japan ............................ 55-181394

[51] Int. Cl.³ ........................ H01M 4/90; H01M 4/96
[52] U.S. Cl. ........................................ 429/42; 429/43
[58] Field of Search ................................. 429/42, 43

[56] References Cited

U.S. PATENT DOCUMENTS

| 3,276,909 | 10/1966 | Moos | 136/86 |
|---|---|---|---|
| 3,329,530 | 7/1967 | Kometani et al. | 429/42 |
| 3,410,727 | 11/1968 | Jasinski | 429/43 |
| 3,444,004 | 5/1969 | Smith | 429/42 |
| 3,591,421 | 7/1971 | Schultze et al. | 429/42 |
| 4,341,848 | 7/1982 | Liu et al. | 429/42 |

FOREIGN PATENT DOCUMENTS 2404312  5/1979  France ................................ 429/42

Primary Examiner—Donald L. Walton
Attorney, Agent, or Firm—Schwartz, Jeffery, Schwaab, Mack, Blumenthal & Koch

[57] ABSTRACT

An air electrode to be used for carrying out electrochemical reduction of an oxygen gas, which comprises an electrode body composed of a porous body and a fluorine-containing solvent incorporated therein. The air electrode is suitable for use in a hydrogen/oxygen fuel cell, a metal/air cell or an oxygen sensor.

18 Claims, No Drawings

AIR ELECTRODE

BACKGROUND OF THE INVENTION

The present invention relates to an air electrode, more specifically to an air electrode suitable for use in a hydrogen/oxygen fuel cell, a metal/air cell or an oxygen sensor.

There have hitherto been used gas diffusion electrodes for air electrodes such as various fuel cells, air-metal cells typically including air/zinc cells, and Galvanic oxygen sensors. In the initial period, thick and uniformly porous electrodes were used as the gas diffusion electrodes, in many cases. However, in order to satisfy the requirements for thinness and leakage-proofing, it has recently become common to use a dual electrode prepared by integrating an electrode body and a hydrophobic layer and adapted to carry out an electrochemical oxygen reduction reaction (Japanese Patent Publication No. 25684/1968).

Namely, in such air electrodes, it has been common to use as the hydrophobic layer, a fluorine-containing resin such as a polytetrafluoroethylene, a polytetrafluoroethylene-hexafluoropropylene copolymer, or a polyethylene-tetrafluoroethylene copolymer, or polypropylene, in a form of a porous material including, for instance, a sintered powder material having a particle size of from 0.2 to 40μ, a paper-like non-woven fabric material prepared by heat treatment of fibers, a similar woven fabric material, a powder material partially replaced by a fluorinated graphite, a film material prepared by rolling fine powder together with a pore-increasing agent or a lubricant oil, followed by heat treatment, or a film material prepared by rolling without being followed by heat treatment (Japanese Patent Publication No. 44978/1973). Further, in a case where no fluid leakage is allowed, for instance, in the case of an air electrode for Galvanic oxygen sensor to be used for detecting the concentration of oxygen gas dissolved in water, a thin gas-permeable non-porous film resistant to an electrolyte has been used on the gas side. An air electrode used has been constructed by integrating such a water repellent layer or gas permeable film and a porous electrode as the electrode body by pressing or by means of an adhesion, or by coating such a water repellent layer with an electrode body-forming material (Battery Handbook, Denki Shoin, P. 2–135).

The electrode body in this case is formed by integrating active carbon powder carrying a catalyst such as nickel tungstate having a low oxygen reduction overvoltage, tungsten carbide coated with palladium-cobalt, nickel, silver, platinum or palladium, with a porous metal body, a porous carbon body or a non-woven carbon fiber fabric, with use of a binder such as polytetrafluoroethylene.

However, there still remain some problems with the conventional air electrode, e.g., a thin air electrode for an air/zinc cell where it is required to be thin, completely free from fluid leakage and useful for heavy duty discharge.

For instance, in the case where a porous body prepared by sintering a fluorine-containing resin powder is used as the hydrophobic layer, continuous discharge under fairly heavy duty at a level of about 20 mA/cm$^2$ can be done, but the thickness is required to be at a level of from 0.125 to 0.50 mm, and since the pore sizes are not uniform and there exist pores of large diameters, it is likely that due to, e.g., the volume expansion at the opposite electrode to the air electrode, the inner pressure of the cell increases, thus leading to fluid leakage, especially in the case of a sealed type. On the other hand, in an air electrode wherein a thin gas permeable non-porous film is provided at the gas side, e.g., by means of an adhesive or the like, to prevent fluid leakage, it is possible to completely prevent fluid leakage, and to make the thickness as thin as about 12.5 μm. In this case, however, it would become highly difficult to carry out continuous discharge at a large current at a level of at least 10 mA/cm$^2$.

Further, there has been known a so-called teflon-bonded air electrode in which carbon or nickel powder is used as the major component and PTFE (polytetrafluoroethylene) powder is dispersed therein. However, in such an electrode, a hydrophilic surface is exposed to a substantial extent and an electrolyte tends to gradually penetrate into the electrode through the surface, whereupon no sufficient diffusion of the gas into the electrode will be done. Thus, it has a drawback that the stability of the heavy duty characteristic of the electrode is thereby impaired.

It is conceivable that this is caused as follows: the PTFE used as the binder is hardly soluble in a solvent such as water, and it is used in a form of powder or a dispersion. However, the minimum size of the PTFE particles in the dispersion is at a level of about 0.2 μm, and it is difficult to obtain a dispersion of particles having smaller size. Accordingly, unless the size of pores in the active carbon or porous sintered material is sufficiently large relative to the particle size of the PTFE, penetration of the PTFE particles into the pores can not be expected. Thus, a hydrophilic surface would remain in the electrode. It has been proposed to enlarge the size of pores of the porous sintered material to a level greater than the size of the dispersed PTFE particles so as to permit the PTFE particles to penetrate deeply into the pores.

However, if the size of the pores of the electrode is so enlarged, the structure of the three phase interface effective for discharge reaction becomes coarse, and the surface area is decreased, whereupon it becomes impossible to obtain a large current. Besides, no penetration into fine pores such as pores of the active carbon is expected. Thus, there has not yet been found one which exhibits adequate characteristics for practical purposes.

SUMMARY OF THE INVENTION

Under these circumstances, the present inventors have found that, in an electrochemical reduction reaction of an oxygen gas in the electrode which takes place at the microscopic three phase interface composed of a gaseous phase of diffused air from the atmosphere, a solid phase of the electrode body and a liquid phase of an electrolyte, it is possible to accelerate the reaction by (1) increasing the oxygen concentration (partial pressure) at the microscopic three phase interface and (2) increasing the rate of the electrochemical reduction reaction of the oxygen gas, which fact enables heavy duty discharge. Thus, the present invention has been accomplished.

In view of the foregoing points, it is an object of the present invention to provide an air electrode which can readily be made thin, which is useful for heavy duty discharge and which is capable of certainly preventing fluid leakage.

Firstly, the gist of the present invention resides in that the above mentioned oxygen concentration in the vicinity of the microscopic three phase interface can be increased by incorporating a fluorine-containing solvent into the electrode body adapted to carry out an electrochemical reduction reaction of an oxygen gas, and the water repellent property can thereby be effectively improved, whereby it is possible to remarkably improve the heavy duty discharge characteristics and the fluid leakage-proofing property.

DETAILED DESCRIPTION OF PREFERRED EMBODIMENTS

The fluorine-containing solvent which may be used in the present invention, is liquid at room temperature, has a relatively high boiling point and oxygen-dissolving power, and has a relatively low surface tension. Further, in regard to the fluorine-containing solvent, its boiling point is generally within the range of from 50° to 350° C., preferably from 100° to 300° C., and most preferably from 150° to 260° C.; its oxygen-dissolving power is generally not less than 15%, preferably not less than 25%, most preferably not less than 40% by volume; and its surface tension is generally not more than 50, preferably not more than 40, most preferably not more than 30 dyne/cm. As concrete examples of the fluorine-containing solvent used in the present invention, there are enumerated a low polymer of 1-chloro-1,2,2-trifluoroethylene; perfluoro alkanes such as perfluoropentane and perfluorohexane; perfluoro alkenes such as $CF_3-CF=CF-CF_3$; cyclic fluoride compounds such as tetrachlorobenzene and perfluoro-1,3,5-trimethylcyclohexane; perfluorohydride such as $H(CF_2)_2F$; perfluorocarboxylic acids such as $H(CF_2CF_2)_nCOOH$ (n=3 to 30); perfluoroketones; perfluoroaldehydes; perfluoroalcohols; perfluoroethers such as $C_4F_9O$; amine fluorides such as $(C_3F_7)NC_4F_9$; perfluorothiol; perfluorosulfonic acid; and organic-phosphorus compound-arsenic compound-fluorine derivatives. However, the above-mentioned low polymer of 1-chloro-1,2,2-trifluoroethylene (degree of polymerization: 4 to 8, and molecular weight; 500 to 900) is particularly suitable for the objects of the present invention, because its oxygen-dissolving power is about ten times larger than that of water and it is excellent in alkali resistance, acid resistance and thermal resistance. These solvents just described above may be employed alone or in combinations of two or more thereof.

As the electrode body used in the present invention, there is employed a porous body composed of active carbon, graphite, porous sintered material of metal powder such as nickel, or porous sintered material of PTFE. A pore size of the porous materials is generally within from 0.05 to 200 $\mu$m, but with use of a porous material having a pore size of from 0.1 to 10 $\mu$m, the removal rate of the ions produced by the reduction of oxygen is facilitated, whereby an electric current having a great current density can readily be taken out and the uniformity of the water repellent layer is further improved and the mechanical strength is thereby improved.

Further, the fluorine-containing solvent is added in an amount of generally at least 0.0001% by weight relative to the amount of the porous body to be adequately effective for the purpose of the present invention, and it is desirable in practice that the amount is below 30% by weight to suppress the internal resistance of the electrode body and thereby to prevent the voltage drop due to the heavy duty discharge. An amount of the fluorine-containing solvent to be added is preferably within 0.001 to 20% by weight relative to the porous body. In the case where the active carbon is used as a porous body, the amount thereof is generally within from 0.0001 to 25% by weight relative to the weight of the active carbon, preferably from 0.001 to 15% by weight.

As described above, with use of an air electrode in which a fluorine-containing solvent is incorporated in the electrode body, it is possible to increase the oxygen concentration within the electrode and to obtain a heavy duty discharge characteristic of at least about 45 mA/cm². Further, the fluorine-containing solvent used in the present invention has a relatively low molecular weight (as compared with PTFE), and accordingly can readily penetrate even into fine pores of the active carbon, whereby the hydrophobic property can remarkably improved and an air electrode having a superior fluid leakage-proofing property is obtainable.

Further, the electrode body which is used in the present invention is composed, of e.g., active carbon or graphite, and with use of a porous material having a pore size of from 0.1 to 10 $\mu$m, the removal rate of the ions produced by the reduction of oxygen is facilitated, whereby an electric current having a great current density can readily be taken out and the uniformity of the water repellent layer is further improved and the mechanical strength is thereby improved.

Further, according to the present invention, by incorporating a catalyst for an oxygen reduction reaction concomitantly with the fluorine-containing solvent into the electrode body, it is possible to further improve the heavy duty discharge characteristics and to obtain an air electrode having a superior fluid leakage-proofing property. Namely, the fluorine-containing solvent is adsorbed on the surface of the catalyst for the oxygen reduction reaction, which is composed of a metal, a metal compound or an organic compound, thereby to form a thin liquid film. This liquid film of the fluorine-containing solvent has a high oxygen dissolving power and it takes in oxygen, and increases the oxygen concentration in the vicinity of the above mentioned microscopic three phase interface, and further the reduction reaction of oxygen is facilitated by the catalytic activity, whereby an electrode having a superior heavy duty discharge characteristic of at least about 50 mA/cm² is obtainable. As the catalyst for the oxygen reduction reaction, a metal (such as Ag or Ni), a metal compound such as a metal oxide (such as $MnO_2$, $Ag_2O$ or $Co_2O_3$) or a metal hydroxide (such as NiOOH or CoOOH), and an organic compound, may be used. The amount thereof may be suitably adjusted, but it is preferred for practical purposes that the amount is about 10% relative to the weight of the porous body.

Especially when continuous discharge with a great current density is required, the catalyst for the oxygen reduction reaction is selected from various metallophthalocyanines metalloporphyrins, and dimers of metalloporphyrins such as iron phthalocyanine, cobalt phthalocyanine, cobalt porphyrin, a dimer of cobalt porphyrin and a dimer of iron porphyrin, and it is added in an amount of from 1 to 20% relative to the weight of the porous body, whereby adequate catalytic activity and oxygen adsorption ability are obtainable.

Further, in the case where the dimer of a metalloporphyrin is used, four electron reduction takes place simultaneously, as compared with the case of two electron reduction in a usual oxygen reduction catalyst, and accordingly, the oxygen reduction reaction is thereby facilitated to present a particularly superior heavy duty discharge characteristic.

Thus, by concomitantly incorporating the fluorine-containing solvent and the oxygen reduction catalyst into the electrode body, the oxygen concentration in the electrode can be increased, and the oxygen reduction reaction can be facilitated, whereby an air electrode having a superior heavy duty discharge characteristic and a superior fluid leakage proofing property by virtue of the presence of the fluorine-containing solvent, is obtainable.

Further, according to the present invention, it is possible to increase the oxygen concentration in the vicinity of the above-mentioned microscopic three phase interface by incorporating the fluorine-containing solvent and a perfluoro compound in the electrode body for carrying out the electrochemical reduction of an oxygen gas. Further, by the presence of the perfluoro compound, the rate of donating and accepting the taken-in oxygen is remarkably facilitated, whereby the heavy duty discharge characteristic can be improved to a great extent. Further, by the concomitant incorporation of the perfluoro compound with the fluorine-containing solvent, the water repellent property is further improved, whereby the fluid leakage-proofing property can be improved. Namely, the fluorine-containing solvent containing the perfluoro compound is adsorbed on the surface of, e.g., active carbon constituting the electrode body, to form a thin liquid film. The perfluoro compound contained in this thin liquid film has a high oxygen dissolving power and is capable of feeding oxygen in the air electrode to the surface of, e.g., active carbon, and it has a high oxygen donating and accepting rate, whereby a heavy duty discharge characteristic as high as at least about 50 mA/cm$^2$ is obtainable. Further, the water repellent property is further improved by the perfluoro compound, whereby the fluid leakage-proofing property can be improved.

The perfluoro compounds used in the present invention are molecules having a large electron affinity in which there is dissolved oxygen having a lower ionization potential compared with other gases such as nitrogen, and a typical compound of them is fluoro-carbon. The reason why the fluoro-carbon allows the oxygen gas to selectively dissolve therein is that the oxygen having a lower ionization potential is stabilized in a solution in accordance with a magnitude of the electron affinity of a fluorine atom contained therein. The perfluoro compounds are different from the above-mentioned fluorine-containing solvents in an oxygen donating and accepting ring, that is to say, as understood from the fact that these compounds are used by way of artificial blood [(Harumasa Oyagi, Breath and Circulation 22 (3), 4 (1974)], the oxygen donating and accepting rate of the compounds is as fast as less than 100 msec.

As the perfluoro compound which may be used in the present invention, there may be mentioned perfluorotri-n-butylamine (FC-43), perfluoro-tripropylamine (FTPA), perfluorodecalin (FDC), perfluoromethyl-decalin (FMD), or perfluorinated ether (Freon E$_4$). These perfluoro compounds have an oxygen dissolving power as high as at least about 40% by volume, and they have an oxygen donating and accepting rate of from 14 to 26 msec and the reaction is done almost instantly and is reversible.

Moreover, the perfluoro compounds mentioned above may be employed alone or in the form of a mixture of two or more.

Thus, by incorporating the fluorine-containing solvent and the perfluoro compound into the electrode body, the heavy duty discharge characteristic is further improved and the water repellent property is also improved to a large extent by a synergistic effect of the fluorine-containing solvent and the perfluoro compound. Further, the amount thereof is preferably at least 0.1% by volume relative to the amount of the fluorine-containing solvent to attain the effectiveness of the present invention and preferably at most 10% by volume from the practical standpoint.

Further, according to the present invention, an air electrode having a further improved heavy duty discharge characteristic and fluid leakage-proofing property is obtainable by incorporating a catalyst for an oxygen reduction reaction, together with the fluorine-containing solvent and the perfluoro compound, into the electrode body. Namely, the fluorine-containing solvent containing the perfluoro compound is adsorbed on the surface of the catalyst for the oxygen reduction reaction, which is composed of a metal, a metal compound or an organic compound, to form a thin liquid film. The liquid film composed of the fluorine-containing solvent containing the perfluoro compound, has a high oxygen dissolving power, and a characteristic of carrying out the donation and acceptance of oxygen at a high speed. Consequently, the reduction reaction of oxygen is facilitated by the catalyst, whereby a heavy duty discharge characteristic of at least about 55 mA/cm$^2$ is obtainable and the water repellent property can further be improved.

Even in a system in which the fluorine-containing solvent and the perfluoro compound exist together, the catalyst for an oxygen reduction reaction can be used.

As the catalyst for the oxygen reduction reaction, those which are similar to ones mentioned above may be used in a similar amount. However, especially when continuous discharge with a great current density is required, it is preferably selected from various metallophthalocyanines and dimers of metalloporphyrins such as iron phthalocyanine, cobalt phthalocyanine, cobalt porphyrin, a dimer of cobalt porphyrin and a dimer of iron porphyrin.

In the present invention, also in regard to air-zinc cells where sodium hydroxide was used as the electrolyte and other cells where there are used other electrolytes such as solutions of ammonium chloride or potassium hydroxide, or solutions obtained by mixing, lithium hydroxide, cesium hydroxide, rubidium hydroxide, etc. with the above-mentioned solutions, similar results are, needles to say, obtained. Further, the electrode of the present invention is also applicable to an air-iron cell etc.

As described in detail in the foregoing, according to the present invention, an air electrode which is thin and capable of a heavy duty discharge and which is highly resistant to fluid leakage, can readily be obtained, and accordingly, the present invention has a great value for industrial applications.

Now, the invention will be described in detail with reference to the Examples and Comparative Examples.

EXAMPLES 1 TO 9

Active carbon powder as an electrode body-forming material to which various catalysts for the oxygen reduction reaction were added or not added, was subjected to adsorption treatment with a solution of a low molecular weight polymer (n=4 to 6, molecular weight: 500 to 700) of ethylene trifluorochloride containing or not containing a perfluoro compound, and from 10 to 20% by weight of a 60% dispersion of polytetrafluoroethylene resin (PTFE) as a binder was added thereto, kneaded and spread to form sheets, which are then pressed on each side of a nickel net to obtain an air electrode body having a thickness of about 0.7 mm (a solution adsorption method). Then, a composite thin film having a thickness of 6 μm composed of a lamination of polytetrafluoroethylene (PTFE) as a water repellent layer and fluoroethylenepropylene (FEP) as a heat fusable adhesive layer, is fused to the electrode body by being heated at 250° C. to obtain an air electrode having an overall thickness of about 0.7 mm.

EXAMPLES 10 TO 15

Active carbon powder as an electrode body-forming material to which various catalysts for the oxygen reduction reaction were added or not added, was mixed with from 10 to 20% by weight of a 60% dispersion of polytetrafluoroethylene resin (PTFE) as a binder, kneaded and spread to form sheets, which are then pressed on each side of a nickel net to obtain an electrode body having a thickness of about 0.7 mm. Then, this electrode body was subjected to a vacuum immersion in a solution of a low molecular weight polymer (n=4 to 6, molecular weight of 500 to 700) of ethylene trifluorochloride containing or not containing a perfluoro compound (a vacuum immersion method in a solution), and dried at 60° C. to obtain an air electrode body, which was then made into an air electrode having an overall thickness of about 0.7 mm in a manner similar to Example 1.

EXAMPLES 16 TO 26

Active carbon powder as an electrode body-forming material to which various catalysts for the oxygen reduction reaction were added or not added, was fed into a rotary evaporator and subjected to a gaseous phase adsorption with a solution of a low molecular weight polymer (n=4 to 6, molecular weight: 500 to 700) of ethylene trifluorochloride containing or not containing a perfluoro compound in a vacuum of 2 mmHg (25° C.) for 5 hours (a gaseous phase adsorption method). With use of this active carbon powder, an air electrode having an overall thickness of about 0.7 mm was prepared in a manner similar to Example 1.

COMPARATIVE EXAMPLE 1

A catalyst-containing active powder prepared by dispersing active carbon powder in an aqueous solution of palladium chloride and reducing it with formalin, was subjected to water-proofing treatment with a 10 to 15% by weight of a 60% dispersion of polytetrafluoroethylene resin (PTFE), to obtain a water proof catalyst powder. PTFE as a binder was mixed therewith and formed into a sheet, which was pressed on a nickel net to obtain an air electrode body having a thickness of about 0.6 mm. On the other hand, a PTFE resin dispersion was mixed with an artificial graphite powder, and the mixture was subjected to heat treatment, to obtain a water proof graphite powder. PTFE as a binder was added thereto and formed into a sheet, which was overlaid and pressed on the above electrode body and subjected to heat treatment to obtain an air electrode having a double layer structure and having an overall thickness of about 1.6 mm.

COMPARATIVE EXAMPLE 2

In a manner similar to Example 2, active carbon powder incorporated with 10% by weight of cobalt phthalocyanine as a catalyst for the oxygen reduction reaction, was formed into a sheet with use of polytetrafluoroethylene as a binder, and an electrode body having a thickness of about 0.7 mm was prepared. This electrode body was formed into an air electrode having an overall thickness of about 0.7 mm in a manner similar to Example 1 without immersion with a low molecular weight polymer of ethylene trifluorochloride.

COMPARATIVE EXAMPLE 3

In a manner similar to Example 2, active carbon powder incorporated with 5% by weight of a dimer of cobalt porphyrin as a catalyst for the oxygen reduction reaction, was formed into a sheet with use of polytetrafluoroethylene as a binder, and an electrode body having a thickness of about 0.7 mm was prepared. This electrode body was formed into an air electrode having an overall thickness of about 0.7 mm in a manner similar to Example 1 without immersion with a low molecular weight polymer of ethylene trifluorochloride.

In the above Examples and Comparative Examples, air electrodes were prepared with use of various catalysts for the oxygen reduction reaction and various perfluoro compounds, and in order to investigate their performance, an air-zinc cell was assembled using a non-woven fabric of polyamide as a separator and a zinc electrode as the opposite electrode, said zinc electrode having been prepared by dispsersing zinc powder amalgamated with 3% of mercury and having a particle size of from 60 to 150 mesh in a gelled electrolyte prepared by dispersing a gelation agent in a sodium hydroxide solution.

Such air-zinc cells were left to stand in air at 25° C. for 16 hours, and then discharged at various currents for 5 minutes, and the electric current values at which the terminal voltages after the 5 minutes were at most 1.0 V were measured. On the other hand, the air-zinc cells were stored in a relative humidity of 90% at a temperature of 45° C. and the fluid leakage was observed. The results thereby obtained are shown in Table 1.

TABLE 1

| | Composition | | Current density (mA/cm$^2$) | Number of days till leakage occurred |
|---|---|---|---|---|
| | Catalysts for the oxygen reduction reaction | Perfluoro compounds | | |
| Example | | | | |
| 1 | — | — | 50 | 72 |
| 2 | 10 wt % MnO$_2$ | — | 55 | 71 |
| 3 | 1 wt % Co—phthalocyanine | — | 65 | 73 |
| 4 | 5 wt % Dimer of Co—porphyrin | — | 67 | 73 |
| 5 | — | Perfluorodecalin | 54 | 75 |

TABLE 1-continued

| | Composition | | Current density (mA/cm$^2$) | Number of days till leakage occurred |
|---|---|---|---|---|
| | Catalysts for the oxygen reduction reaction | Perfluoro compounds | | |
| 6 | 10 wt % MnO$_2$ | Perfluorodecalin | 62 | 74 |
| 7 | 1 wt % Co—phthalocyanine | Perfluorodecalin | 70 | 78 |
| 8 | 1 wt % Fe—phthalocyanine | Perfluorodecalin | 68 | 78 |
| 9 | 5 wt % Dimer of Co—porphyrin | Perfluorodecalin | 72 | 80 |
| 10 | — | — | 45 | 70 |
| 11 | 10 wt % MnO$_2$ | — | 52 | 70 |
| 12 | 1 wt % Co—phthalocyanine | — | 60 | 70 |
| 13 | — | Perfluoro-tri-n-butylamine | 49 | 72 |
| 14 | 10 wt % MnO$_2$ | Perfluoro-tri-n-butylamine | 55 | 71 |
| 15 | 1 wt % Co—phthalocyanine | Perfluorodecalin | 65 | 76 |
| 16 | — | — | 60 | 65 |
| 17 | 10 wt % MnO$_2$ | — | 65 | 64 |
| 18 | 1 wt % Ag | — | 63 | 65 |
| 19 | 1 wt % Co—phthalocyanine | — | 75 | 67 |
| 20 | 5 wt % Dimer of Co—porphyrin | — | 77 | 68 |
| 21 | — | Perfluoro-tri-n-butylamine | 64 | 70 |
| 22 | — | Perfluorodecalin | 65 | 70 |
| 23 | 10 wt % MnO$_2$ | Perfluorodecalin | 70 | 68 |
| 24 | 1 wt % Co—phthalocyanine | Perfluorodecalin | 80 | 72 |
| 25 | 1 wt % Fe—phthalocyanine | Perfluoro-tri-n-butylamine | 78 | 72 |
| 26 | 5 wt % Dimer of Co—porphyrin | Perfluorodecalin | 82 | 73 |
| Comparative Example | | | | |
| 1 | | | 25 | 20 |
| 2 | | | 45 | 20 |
| 3 | | | 47 | 20 |

It is apparent from the above Table that with use of the air electrodes according to the present invention, a heavy duty discharge can be done, and the leakage-proof characteristic can be improved.

We claim:

1. An air electrode for use in carrying out electrochemical reduction of an oxygen gas, which comprises an electrode body comprised of a porous body and a fluorine-containing solvent incorporated therein, said fluorine-containing solvent being a liquid at room temperature and having a boiling point of from about 50° to 350° C., an oxygen-dissolving power of at least about 15% by volume, and a surface tension of not greater than about 50 dyne/cm.

2. An air electrode as claimed in claim 1, wherein said fluorine-containing solvent has a boiling point of from 50° to 350° C., an oxygen-dissolving power of at least 15% by volume, and a surface tension of not greater than 50 dyne/cm.

3. An air electrode as claimed in claim 1, wherein said fluorine-containing solvent has a boiling point of from 100° to 300° C., an oxygen-dissolving power of at least 25% by volume, and a surface tension of not greater than 40 dyne/cm.

4. An air electrode as claimed in claim 3, wherein said fluorine-containing solvent is selected from the group consisting of fluorohalogenides; perfluoro alkanes; perfluoro alkenes; cyclic fluoride compounds; perfluorohydrides; perfluorocarboxylic acids; perfluoroketones; perfluoroaldehydes; perfluoroalcohols; perfluoroethers; amine fluorides; perfluorothiols; perfluorosulfonic acids; and organic-phosphorus compound-arsenic compound-fluorine derivatives.

5. An air electrode as claimed in claim 4, wherein said fluorine-containing solvent is selected from the group consisting of a low polymer of 1-chloro-1,2,2-trifluoroethylene, perfluoropentane, perfluorohexane, CF$_3$-CF=CF-CF$_3$, tetrafluorobenzene, perfluoro-1,3,5-trimethylcyclohexane, H(CF$_2$)$_2$F, H(CF$_2$CF$_2$)$_n$-COOH (n=3 to 30), C$_4$F$_9$O and (C$_3$F$_7$)$_2$NC$_4$F$_9$.

6. An air electrode as claimed in claim 5, wherein said fluorine-containing solvent is a low polymer of 1-chloro-1,2,2-trifluoroethylene.

7. An air electrode as claimed in claim 1, wherein an amount of the incorporated fluorine-containing solvent is from 0.0001 to 30% by weight relative to the weight of the porous body.

8. An air electrode for use in carrying out electrochemical reduction of an oxygen gas, which comprises an electrode body comprised of a porous body having incorporated therein a fluorine-containing solvent and a perfluoro compound.

9. An air electrode as claimed in claim 8, wherein said perfluoro compound is an amine fluoride, a cyclic fluoride compound, and a perfluoroether.

10. An air electrode as claimed in claim 9, wherein said perfluoro compound is selected from the group consisting of perfluoro-tri-n-butylamine (FC-43), perfluoro-tripropylamine (FTPA), perfluorodecaline (FDC), perfluoromethyldecalin (FMD), and perfluorinated ether (Freon E$_4$).

11. An air electrode as claimed in claim 8, wherein an amount of the incorporated fluoro compound is from 0.1 to 10% by volume relative to the weight of said fluorine-containing solvent.

12. An air electrode as claimed in claim 8, wherein a catalyst for an oxygen reduction reaction is concomitantly incorporated in said electrode body.

13. An air electrode as claimed in claim 12, wherein said catalyst for the oxygen reduction reaction is at least one selected from a metallophthalocyanine, a metalloporphyrin and a dimer of metalloporphyrin.

14. An air electrode as claimed in claim 8, wherein said porous body is made of active carbon.

15. An air electrode as claimed in claim 1, wherein a catalyst for an oxygen reduction reaction is concomitantly incorporated in said electrode body.

16. An air electrode as claimed in claim 1, wherein said catalyst for the oxygen reduction reaction is at least one selected from a metallophthalocyanine, metalloporphyrin and a dimer of metalloporphyrin.

17. An air electrode as claimed in claim 1, wherein said porous body is made of active carbon.

18. An air electrode as claimed in claim 2, wherein said fluorine-containing solvent is a liquid at room temperature.

* * * * *